US008039609B2

(12) United States Patent
Missailidis et al.

(10) Patent No.: US 8,039,609 B2
(45) Date of Patent: Oct. 18, 2011

(54) APTAMERS DIRECTED TO MUC1

(75) Inventors: Sotiris Missailidis, Milton Keynes (GB); Jean Gariepy, Ontario (CA); Catia Sofia Matos Ferreira, Ontario (CA)

(73) Assignees: The Open University (GB); The University Health Network (CA)

( * ) Notice: Subject to any disclaimer, the term of this patent is extended or adjusted under 35 U.S.C. 154(b) by 0 days.

(21) Appl. No.: 12/299,596

(22) PCT Filed: May 2, 2007

(86) PCT No.: PCT/GB2007/050234
§ 371 (c)(1),
(2), (4) Date: Jun. 22, 2009

(87) PCT Pub. No.: WO2007/129114
PCT Pub. Date: Nov. 15, 2007

(65) Prior Publication Data
US 2009/0286854 A1    Nov. 19, 2009

(30) Foreign Application Priority Data

May 4, 2006    (GB) .................................. 0608778.7

(51) Int. Cl.
*C07H 21/04* (2006.01)
(52) U.S. Cl. ................... 536/24.5; 536/24.31; 536/24.1; 514/44; 435/6; 435/325; 435/375
(58) Field of Classification Search .................. None
See application file for complete search history.

(56) References Cited

U.S. PATENT DOCUMENTS

2006/0292643 A1   12/2006  Goletz et al.

FOREIGN PATENT DOCUMENTS

| WO | WO-03/003985 A2 | 1/2003 |
|---|---|---|
| WO | WO-2004/014954 A1 | 2/2004 |
| WO | WO-2004/022590 A2 | 3/2004 |
| WO | WO-2004/065423 A2 | 8/2004 |
| WO | WO-2004/081574 A2 | 9/2004 |
| WO | WO-2005/019429 A2 | 3/2005 |
| WO | WO-2005/111238 A2 | 11/2005 |

OTHER PUBLICATIONS

"Great Britain Application Serial No. GB0608778.7, Search Report dated Aug. 21, 2006", 1 pg.
"International Application Serial No. PCT/GB2007/050234, International Search Report mailed Jan. 29, 2008", 7 pgs.
"International Application Serial No. PCT/GB2007/050234, Written Opinion mailed Jan. 29, 2008", 10 pgs.
Bäckström, M., et al., "Recombinant MUC1 mucin with a breast cancer-like 0-glycosylation produced in large amounts in Chinese-hamster ovary cells", *Biochemical Journal*, 376(3), (Dec. 2003), 677-686.
Brokx, R. D, et al., "Nuclear Magnetic Resonance-Based Dissection of a Glycosyltransferase Specificity for the Mucin MUC1 Tandem Repeat", *Biochemistry*, 42(47), (Dec. 2003), 13817-13825.
Fereira, C., et al., "DNA aptamers that recognize the MUC1 tumor marker (Poster No. 49)", *European Journal of Cancer.Supplement*, vol. 2(8), (Sep. 2004), p. 19.
Mcdermott, K. M., et al., "Overexpression of MUCI Reconfigures the Binding Properties of Tumor Cells", *Int. J. Cancer*, 94, (2001), 783-791.
Missailidis, S, et al., "Selection of aptamers with high affinity and high specificity against C595, an anti MUC1 IgG3 monoclonal antibody, for antibody targeting", *Journal Of Immunological Methods*, 296(1-2), (Jan. 2005), 45-62.
Mueller, S, et al., "Recombinant MUC1 Probe Authentically Reflects Cell-Specific 0-Glycosylation Profiles of Endogenous Breast Cancer Mucin. High Density and Prevalent Core 2-Based Glycosylation", *Journal of Biological Chemistry*, 277(29), (Jul. 2002), 26103-26112.
Olson, F. J, et al., "A MUC1 tandem repeat reporter protein produced in CHO-K1 cells has sialylated Core 1 0-glycans and becomes more densely glycosylated if coexpressed with polypeptide-GaINAc-T4 transferase", *Glycobiology*, 15(2), (Feb. 2005), 177-191.
Rughetti, A., et al., "Regulated expression of MUC1 epithelial antigen in erythropoiesis", *British Journal of Haematology*, 120, (2003), 344-352.
Tuerk, C., et al., "Systematic Evolution of Ligands by Exponential Enrichment: RNA Ligands to Bacteriophage T4 DNA Polymerase", *Science*, 249(3), (Aug. 1990), 505-510.

*Primary Examiner* — Kimberly Chong
(74) *Attorney, Agent, or Firm* — Schwegman, Lundberg & Woessner, P.A.

(57) ABSTRACT

Aptamers against the glycosylated form of MUC1 are described, along with their use in treatment and diagnosis of conditions associated with elevated production of MUC1.

15 Claims, 5 Drawing Sheets

|  | 5RT-T1 | 5RT-T2 | 5RT-T3 | 5RT-T4 | 5RT-T5 | 5RT-T6 | 5RT-T7 |
|---|---|---|---|---|---|---|---|
| INITIAL | 25 | 20.9 | 28.8 | 23.8 | 40.7 | 26 | 16.2 |
| WASH | 1 | 1.1 | 0 | 0.9 | 0.7 | 3.3 | 2.2 |
| BOUND | 24 | 19.8 | 28.8 | 22.9 | 40 | 22.7 | 14 |

*FIG. 4B*

APTAMERS DIRECTED TO MUC1

RELATED APPLICATIONS

This application is a nationalization under 35 U.S.C. 371 of PCT/GB2007/050234, filed May 2, 2007 and published as WO 2007/129114 A2, on Nov. 15, 2007, which claimed priority under 35 U.S.C. 119 to United Kingdom Patent Application Serial No. 0608778.7, filed May 4, 2006; which applications and publication are incorporated herein by reference and made a part hereof.

FIELD OF THE INVENTION

The present invention relates to the generation of aptamers that recognise the glycosylated and unglycosylated form of the MUC1 tumour marker, to the aptamers themselves, and to uses and methods involving such aptamers.

BACKGROUND TO THE INVENTION

Cancer is a leading cause of morbidity in the world. Work has been carried out for many years on the identification of molecules that are characteristic of the disease. Many have been found to be unique in tumours or are overexpressed, altered or otherwise differing in cancer. Such tumour markers are used as targets in the many immunological approaches to cancer diagnosis and therapy.

The MUC1 protein is one such marker that is known to be overexpressed in malignant cells. This epithelial mucin is coded for by the MUC1 gene. It is not a classic extracellular complex mucin, such as those found as major components of the mucous layers covering the gastro-intestinal and respiratory tracts, but is a transmembrane molecule, expressed by most glandular epithelial cells. The protein consists of a number of distinct regions, including an N-terminus with a putative signal peptide and degenerate tandem repeats, a transmembrane region and a C-terminus cytoplasmic tail. The major portion of the protein is the tandem repeat region. This consists of degenerate repeats of the unique peptide sequence APDTRPAPGSTAPPAHGVTS. The number of repeats varies with the allele, thus making the gene and protein highly polymorphic. MUC1 is also referred to as MUC-1, mucin 1, muc-1, episialin, peanut-reactive urinary mucin (PUM), polymorphic epithelial mucin (PEM), CD227, epithelial membrane antigen (EMA), DF3 antigen and H23 antigen.

MUC1 mucin is restricted to the apical cell surface by interactions with the microfilament network. Although MUC1 is widely expressed by normal glandular epithelial cells, the expression is dramatically increased when the cells become malignant. This has been well documented for breast and ovarian cancer, as well as some lung, pancreatic and prostate cancers. Recently it has also been shown that MUC1 is a valuable marker for bladder cancer and has been used for its diagnosis in a number of studies. Antibody studies have also shown not only that MUC1 is overexpressed in carcinomas but also that the pattern of glycosylation is altered. Thus, in the breast cancer mucin, glycosylation changes result in certain epitopes in the core protein being exposed which are masked in the mucin produced by the lactating mammary gland. These characteristics of MUC1 have been explored over the years in a number of immunotherapeutic approaches, mainly involving radiolabelled antibodies against breast and bladder cancers. Other attempts on active specific immunotherapies based on MUC1 have also taken place in animal models to investigate the efficacy of immunogens based on MUC1.

These immunotherapeutic approaches had some encouraging results and have led to clinical trials both for the vaccine therapies and the antibody treatments. These strategies however are not without problems. The radiolabelled antibody technique is limited to modest (millicurie) radiation doses since the long circulation time of radiolabelled antibodies makes bone marrow toxicity a problem. Another problem is the time period required to produce specific monoclonal antibodies. Additionally, recent attempts to use peptides instead of antibodies have resulted in molecules with very low affinity for the MUC1 mucin.

International patent application WO2004/081574 describes the generation of aptamers to a synthetic MUC1 peptide. The publication describes the generation of aptamers targeted either to a 60-mer peptide consisting of three copies of the repeat sequence APDTRPAPGSTAPPAHGVTS (SEQ ID NO: 12), or to the nine amino acid peptide APDTRPAPG (SEQ ID NO: 13) contained within this sequence. While this approach may generate useful aptamers, it is possible that alternative approaches may be useful in generating aptamers against different epitopes of the MUC1 peptide. Further, the glycosylation pattern of MUC1 in vivo is known to be altered in carcinomas, such that aptamers to an unglycosylated synthetic peptide may not be as efficient at binding to the peptide in vivo as alternative aptamers raised against the tumour-glycosylated MUC1 protein.

The present invention seeks to overcome or alleviate at least some of these problems with the identification of aptamers based on a recombinant MUC1 protein. In preferred embodiments, this recombinant protein has been glycosylated in a way similar to that utilised in nature, offering a further level of improvement in approaching the in vivo conditions in which our aptamers would operate (for example as therapeutics or diagnostics in the body).

The advantage of this invention in relation to existing inventions based on antibodies recognising MUC1 is that the aptamers provide much more specific and stronger binding to the MUC1 target protein, thus becoming more sensitive in recognising the protein in solution, thus offering the potential of significant reduction in the recognition levels of the tumour marker in current diagnostic assay, resulting in more sensitive assay to offer better prognostic/early diagnostic value. Furthermore, when compared with antibodies as therapeutics, aptamers offer little or no immunogenicity, better tumour penetration, rapid clearance through the kidneys and the urine and natural degradation after a certain amount of time.

The invention can be applied commercially in the diagnosis, imaging and treatment of cancer. It consists of a molecule that recognises a tumour marker, a molecule that is characteristic for the tumour cell or in a different form in tumour cells than in normal cells. This tumour marker is expressed on the surface of cancer cells, but it is also shed in the bloodstream. As such, the molecule(s) that constitute the invention have the potential to be used in diagnostic assays/blood tests to provide a prognosis and/or early diagnosis of tumour or metastatic disease. Furthermore, the molecule has the ability to carry to the surface of the tumour cells modalities that can effect cell kill. Thus, coupling of the molecule to chemotherapy or radiotherapy agents can take them specifically to the tumour cell, thus reducing side effects associated with generic treatments. Finally, coupling of the agent to fluorescent, near infrared, MRI or radionuclide ligands can create a powerful imaging agent that would significantly increase imaging sensitivity and image definition.

SUMMARY OF THE INVENTION

The invention is based on the recognition of a tumour marker, termed MUC1, by a novel category of biological therapeutics, called aptamers. The aptamers are able to recognise the marker on the surface of tumour cells and, if appropriately labelled deliver specifically doses of radiation, other imaging agents such as MRI, NIR and fluorescent modalities, or chemotherapy agents for the imaging and/or treatment of cancer through specific killing of the tumour cells only, avoiding unpleasant side effects from damage to the rest of the body. Furthermore, the aptamers can recognise the tumour marker MUC1 when this is present in the blood of patients, in a diagnostic assay that can indicate the onset or recurrence of the disease. Thus, the potential application of this invention is multiple, ranging from improvements on current assays such as the commercially available CA15-3 MUC1 diagnostic assay, to the imaging and treatment of cancer patients with a variety of epithelial tumours, including this of the breast, stomach, kidneys, prostate etc.

We have identified a method of generating aptamers against a glycosylated form of MUC1; this form more closely mimics the form of MUC1 expressed in vivo, particularly by cancerous tissues. It is expected therefore that this method will generate aptamers more suited to clinical or diagnostic use than prior art methods.

According to a first aspect of the present invention, there is provided an aptamer ligand to recombinant MUC1.

Preferably the aptamer comprises an oligonucleotide, and/or the aptamer is an oligonucleotide. The oligonucleotide may be DNA, RNA, and/or may comprise nucleotides other than adenine, cytosine, guanine, thymine, and uracil; these may be modified nucleotides based on these naturally-occurring nucleotides. Alternatively, the aptamer may comprise a peptide, PNA, or other compounds, for example as described in WO2004/081574, the contents of which are incorporated herein by reference. Preferably the aptamer is at least 25 nucleotides in length; preferably the aptamer is 25 nucleotides in length.

Preferably the aptamer comprises a sequence selected from

| | |
|---|---|
| GAAGTGAAAATGACAGAACACAACA | (SEQ ID NO: 1) |
| GGCTATAGCACATGGGTAAAACGAG | (SEQ ID NO: 2) |
| CAAACAATCAAACAGCAGTGGGGTG | (SEQ ID NO: 3) |
| TACTGCATGCACACCACTTCAACTA | (SEQ ID NO: 4) |
| GGGTTATATTACTCGGCCGGTGTAA | (SEQ ID NO: 5) |
| GGCTATAGCACATGGGTAAAACGAC | (SEQ ID NO: 6) |
| GGCGTACGGTAGGCGGGGTCAACTG | (SEQ ID NO: 7) |
| GCTGGGTAAATAGATGATTCCCGGC | (SEQ ID NO: 8) |
| AGTGGTGGTTTTATAAGACTGATAC | (SEQ ID NO: 9) |
| TAGCCTTAATGCCTTTGTAAGGCGA | (SEQ ID NO: 10) |
| CGGTCTACGGAGCCGCGTTAAACTT | (SEQ ID NO: 11) |

The aptamer may consist of any one of SEQ ID NO: 1 to 11; alternatively, the aptamer may include additional sequences. The aptamer may comprise a sequence having at least 95% identity to any one of SEQ ID NO: 1 to 11, or at least 90%, at least 85%, at least 80%, at least 75%, at least 70% sequence identity.

Preferably the aptamer is a ligand to glycosylated MUC1. Alternatively, the aptamer may be a ligand to unglycosylated MUC1. It will be understood that a particular aptamer may have an affinity for both glycosylated and unglycosylated MUC1. Preferably the aptamer has a greater binding affinity to glycosylated MUC1 than to unglycosylated MUC1.

The recombinant MUC1 used in the present invention is a recombinant MUC1 protein with five tandem repeats of SEQ ID NO: 12. Preferably the aptamer has a greater binding affinity to this recombinant MUC1 than to either or both of the 60-mer consisting of three copies of the repeat sequence APDTRPAPGSTAPPAHGVTS (SEQ ID NO: 12), or to the nine amino acid peptide APDTRPAPG (SEQ ID NO: 13). The recombinant MUC1 may be unglycosylated, but is preferably glycosylated.

Preferably the $K_d$ of the aptamer interaction with MUC1 is less than 1000 nM, less than 500 nM, less than 250 nM, preferably less than 200 nM, less than 100 nM, less than 90 nM.

The aptamer may be in association with another active moiety. The aptamer may be covalently bound or conjugated to the other moiety, or may be otherwise associated therewith. The other moiety may be a label, such as a radiolabel, a fluorescent or a luminescent label. The other moiety may be a ligand, such as a further aptamer or an alternative ligand. The other moiety may be an immunoglobulin, or a fragment or portion of an immunoglobulin. The other moiety may be a therapeutic agent; for example, a radiation source; an antibody or fragment or portion; an anticancer therapeutic agent; or another drug or bioactive agent.

The invention further provides an expression vector encoding an aptamer as herein described. Also provided are nucleotide sequences complementary to any of SEQ ID NO:1 to 11; and RNA equivalents of any of SEQ ID NO:1 to 11.

According to an aspect of the present invention, there is provided a method of treatment of a condition associated with MUC1, the method comprising administering an aptamer as herein described to a subject.

The condition is preferably associated with elevated production of MUC1. Conveniently the condition may be selected from cancer, cystic fibrosis, asthma, chronic obstructive lung disease, non-malignant inflammatory epithelial disease, adenocarcinoma, breast cancer, colon cancer, pancreatic cancer, lung adenocarcinoma, non-small cell lung cancer, ovarian cancer, stomach cancer, prostate cancer, endometrial cancer, and colorectal cancer.

The invention further provides a method of diagnosing a condition associated with MUC1, and preferably associated with elevated production of MUC1, the method comprising detecting the binding of an aptamer as herein described to a cell, tissue, or sample. The method may be performed in vivo or in vitro. The binding of the aptamer may be detected in any convenient manner; for example, by detecting a label associated with the aptamer; by imaging the aptamer; or by determining the amount of bound aptamer. Suitable methods are described in WO2004/081574.

According to a further aspect of the present invention, there is provided an aptamer as herein described for use in treatment or diagnosis.

The invention also provides the use of an aptamer as herein described in the manufacture of a medicament for the treatment of a condition associated with MUC1.

The condition is preferably associated with elevated production of MUC1. Conveniently the condition may be selected from cancer, cystic fibrosis, asthma, chronic obstructive lung disease, non-malignant inflammatory epithelial disease, adenocarcinoma, breast cancer, colon cancer, pancreatic cancer, lung adenocarcinoma, non-small cell lung cancer, ovarian cancer, stomach cancer, prostate cancer, endometrial cancer, and colorectal cancer.

The invention also provides the use of an aptamer as herein described in the manufacture of a diagnostic reagent for the detection or diagnosis of a condition associated with MUC1.

The present invention further provides a pharmaceutical composition comprising an aptamer as herein described. The composition may further comprise a pharmaceutically acceptable carrier.

The aptamers of the invention and formulations or compositions thereof may be administered directly or topically (e.g., locally) to the patient or target tissue or organ as is generally known in the art. For example, a composition can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors.

Delivery systems which may be used with the invention include, for example, aqueous and non aqueous gels, creams, multiple emulsions, microemulsions, liposomes, ointments, aqueous and non aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

Generally, an amount between 0.1 mg/kg and 100 mg/kg body weight/day of active ingredients is administered.

The formulations of the invention can be administered in dosage unit formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agent. The pharmaceutical compositions can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, isotonic sodium chloride solution, and an isotonic salt solution containing sodium and potassium chloride. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The compositions of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compositions of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The compositions of the present invention can also be administered to a subject in combination with other therapeutic compounds to increase the overall therapeutic effect. The use of multiple compounds to treat an indication can increase the beneficial effects while reducing the presence of side effects.

Aspects of the present invention use a method of identifying an aptamer ligand to a recombinant protein target, the method comprising the steps of:
a) attaching a recombinant protein target to a solid support;
b) admixing a library of aptamers with the attached target;
c) eluting non-bound aptamers from the solid support;
d) releasing bound aptamers from the attached target;
e) eluting released aptamers from the solid support;
f) amplifying eluted released aptamers; and
g) identifying amplified aptamers.

The recombinant protein is preferably glycosylated.

The recombinant protein is preferably a full-length protein.

The method may further comprise the step of expressing the recombinant protein prior to attaching it to the solid support. The protein may be expressed in a prokaryotic host; conveniently E. coli, although other suitable expression systems will be known to the skilled person.

The method may comprise the step of glycosylating the recombinant protein prior to attaching it to the solid support.

Steps b) to f) may be repeated at least 2, 3, 5, 10 times.

BRIEF DESCRIPTION OF THE DRAWINGS

FIG. 1 shows a) Elution of the 5TR-1 aptamer from the MUC1 5TR affinity column; b) Elution of the 5TR-2 aptamer from the MUC1 5TR affinity column; c) Elution of the 5TR-3 aptamer from the MUC1 5TR affinity column; d) Elution of the 5TR-4 aptamer from the MUC1 5TR affinity column.

DETAILED DESCRIPTION OF THE INVENTION

The invention will now be described further by way of example with reference to the following experimental procedures and results.

Methods

1. Expression and Purification of MUC1 5TR

The protein was produced and purified by a series of simple steps according to the publication: Brokx, R. D. et al. Nuclear Magnetic Resonance-Based Dissection of a Glycosyltransferase Specificity for the Mucin MUC1 Tandem Repeat. Biochemistry 42, 13817-13825 (2003).

In brief glycerol stocks of BL21 E. coli cells (Novagen, USA) bacteria were streaked fresh on a carbenicillin plate, and a single colony picked and used to inoculate a 40 ml starter culture. The starter culture was grown overnight until turbid and inoculum transferred onto LB-carbenicillin flask and incubation at 37° C. and continued until the culture was induced for production of MUC1 with 0.4 mM isopropyl β-$_D$-thiogalactopyranoside (IPTG), with shaking at 25° C. Bacterial pellets were recovered by centrifugation and MUC1 was purified under denaturing conditions.

The pellets were lysed and purified by Nickel NTA agarose (Qiagen, Mississauga, On, Canada). The protein was extensively dialyzed and HPLC purified and freeze-dried. The sample was further analyzed by SDS page and stained with universal dye simply blue (Invitrogen, USA) for the correct band size. The lyophilized powder was theoretically calculated to be 11.800 kD MW and was confirmed by MALDI mass spectroscopy.

2. Expression and Purification of Recombinant ppGalNAc-T1

The recombinant ppGalNAc-T1 gene product was expressed in *Pichia pastoris* strain KM71H. T1 expression was achieved typically by inoculating a single *Pichia* colony from a plate into BMGY media and growing with vigorous shaking at 30° C. until turbid (48 h); the yeast was harvested by brief spinning at 4 krpm for 10 min, RT and the pellet resuspended in one-tenth volume (30-50 mL) of BMMY medium; growth was continued for another 48 h, feeding with additional methanol (0.25 mL of 100%) every 24 h.

The yeast was harvested and the supernatant removed to a measuring cylinder; the pellet may be stored in the cold room for reuse at a later date. The supernatant was then buffered by immediate addition of one-half volume of 3×T1 buffer, mixed thoroughly, filter-sterilized using a Steriflip filter (Millipore, USA) and chilled at 4° C. This solution was concentrated using an Amicon unit with a membrane, 10 kDa cut-off (Viva Science, USA). Enzyme production was monitored by SDS page. The enzyme was found to be stable at 4° C. and it was further utilized for the construction of the Tn antigen.

3. Glycosylation of Recombinant MUC1 5TR with ppGal-NAc-T1: the Tn Antigen

The reaction mix was composed of distilled water, 0.5 M MES buffer, pH 6, 1 M $MgCl_2$, 50 mM UDP-GalNAc, 10 mg/mL MUC1-5TR, 0.2 M $MnCl_2$ and crude T1 enzyme. The reaction mix was incubated at 37° C. in a static incubator for 48 hours or until completion of glycosylation reaction. This protocol has been extensively optimized previously with $MnCl_2$ being critical for the glycosylation reaction. It is believed that this compound is a necessary catalyst to the reaction. The product of the reaction was analyzed by SDS Page gel analysis, on a 4-20% SDS page gel (Invitrogen) and confirmed by Mass spectrometry.

4. Affinity Chromatography In vitro Selection Method

Two affinity chromatography based methodologies for the in vitro selection of aptamers against the 5TR MUC1 recombinant protein were utilised.

The first methodology was based on the immobilisation of the MUC1 protein to an NHS-HiTrap Sepharose activated column (1 ml) (Uppsala, Sweden). The column was functionalised according to manufacturer's instructions. 3 mg of the protein were immobilized to the column matrix and used for aptamer selection. The amount of protein present after the column functionalization was determined by UV spectroscopy according to manufacturer's specifications. Use of the NHS-HiTrap Sepharose activated column allows the immobilisation of the protein to the column via the amino terminus of the protein.

Alternatively, an affinity chromatography method was developed utilising the 6-His Tag present in the 5TR MUC1 recombinant protein. The 6 Histidine tag present in the MUC1 protein construct was linked by a bond to a HisTrap™ Chelating HP Column (GE Healthcare previously Amersham Pharmacia, Sweden). The HiTrap chelating HP columns (1 ml) were packed with chelating Sepharose high performance consisting of highly cross-linked agarose beads to which iminodiacetic acid had been coupled to stable ether groups via a spacer arm. The chelating matrix was charged with 500 µl of 100 mM Nickel solution. Bound target was visualized by SDS Page gel electrophoresis and stripped to test for peptide loading. The column was re-loaded with 1 ml of 10 mg/ml of MUC1 5TR glycosylated and/or 10 mg/ml of MUC1 5TR un-glycosylated. The columns were washed with 5 column volumes of wash buffer and used for selection rounds.

A stringent system of buffers was designed to evolve highly specific ssDNA aptamers. Binding buffer was composed of 100 mM $NaCl_2$, and 5 mM $MgCl_2$, pH 7.4 and selection carried out at 37° C. to obtain aptamers for use in physiological conditions. Wash buffer and elution buffer were composed the same with the sodium chloride composition differing in concentration (0.15 M and 1.5M respectively). A wash step with 5 column volumes of binding buffer to allow for the washing out of weak binders due to increased stress on the interaction caused by the high volume wash preceded a elution step of 1.5 column volumes. The library was screened against the immobilized target—glycosylated 5TR MUC1 peptide for 10 consecutive rounds at room temperature. In between each round the library was desalted with a PD-10 desalting column to remove excess salt in the sample, freeze-dried to reduce sample volume and further amplified to enhance competition by numbers of the bound aptamer moieties. At the last selection round an additional step was added to the selection protocol. The screened library was screened for binding on a HiTrap chelating column, loaded with nickel, and holding 10 mg of un-glycosylated 5TR MUC1 for partitioning of aptamers binding to the core MUC1 peptide (aptamers bound to column) from aptamers binding to the Tn antigen (GalNac sugar aptamers that went through with the wash). This final step allowed for the selection of both MUC1 5TR core aptamer binders and MUC1 5TR Tn antigen binding aptamers.

After 11 rounds of selection the final pools were cloned into a pCR®21.TOPO vector, and clones were further analyzed and sequenced to yield the DNA base composition of the final pool of aptamers. Sequencing was sent to Macrogen (Seoul, Korea). Sequences were aligned and family analyzed by BioEdit sequence alignment editor (Tom Hall, Ibis Therapeutics, Carlsbad, Calif., USA).

5. Cloning and Sequencing of Aptamers after Final Selection Round

The final round DNA pool was amplified once more by PCR and cloned into a pCR®21.TOPO plasmid vector. 50 randomly picked plasmid clones of each selection were sent to be sequenced and further analyzed using BioEdit sequence alignment editor. Ninety percent of round 10 aptamers were represented by the sequences represented below.

6. Affinity Chromatography Characterisation of the Interactions Between Selected Aptamers and the 5TR-MUC1 Protein.

Synthetic aptamers were first screened through the selection column to screen for any non-binding sequences generated due to artefacts in the cloning and sequencing process. Selected aptamers were dissolved in 1× binding buffer (100 mM NaCl, 5 mM $MgCl_2$, pH 7.2) to a final volume of 1 column volume and allowed to incubate with the prepared selection resin at room temperature for 1 hour. After incubation the aptamers were eluted using a salt gradient with initial buffer (1× wash buffer, 150 mM NaCl, 5 mM $MgCl_2$, pH 7.2) and final buffer (1× elution buffer, 1.5 M NaCl, 5 mM $MgCl_2$, pH 7.2), in an FPLC system with a 1 ml/min flow rate.

The selected aptamers were found to elute from the affinity chromatography matrix at 1.35 M NaCl (±0.05 M; see FIG. 1). On similar studies, the well-characterised and commercially available C595 monoclonal antibody was shown to elute from the chromatography matrix at ~0.8 M NaSCN.

7. Characterisation of Aptamer 5TR-MUC1 Using Competition ELISA

Enzyme linked immunosorbent assay was carried out for assessment of binding and epitope characterization. In brief, an ELISA microtitre plate was coated with 5 µg of MUC1 peptide in 100 µL carbonate buffer (0.05 mol/L, pH 9.6) and left overnight at 4° C. Wells were subsequently blocked with 100 µL of PBS containing 1% (w/v) BSA for 1 h at 37° C. Wells were then washed 3 times with 200 µL of PBS containing 0.05% (v/v) tween-20. 50 µL of excess C595 anti-MUC1 monoclonal antibody at a fixed concentration (30 µM in PBS containing 0.05% tween-20 and 1% BSA) was added per well to ensure saturation of all binding sites and was incubated for 1 h at 37° C. The plate was washed and 50 µL of a concentration series of aptamer ranging from 100 nM to 700 nM in buffer containing 100 mM NaCl, 5 mM MgCl$_2$, 100 mM KCl and 5% glycerol was added to each well and allowed to incubate for 1 hour at 37° C. Plate was again washed and 50 µL of an anti-mouse secondary antibody, peroxidase conjugated (Sigma), were added to the plate and incubated again for 1 h at 37° C. Wells were washed a further three times as described above and colour was developed by addition of 2,2'-azino-di-(3-ethyl-benzo-thiozolin sulfonic acid) reagent (Sigma).

Figure 1A:
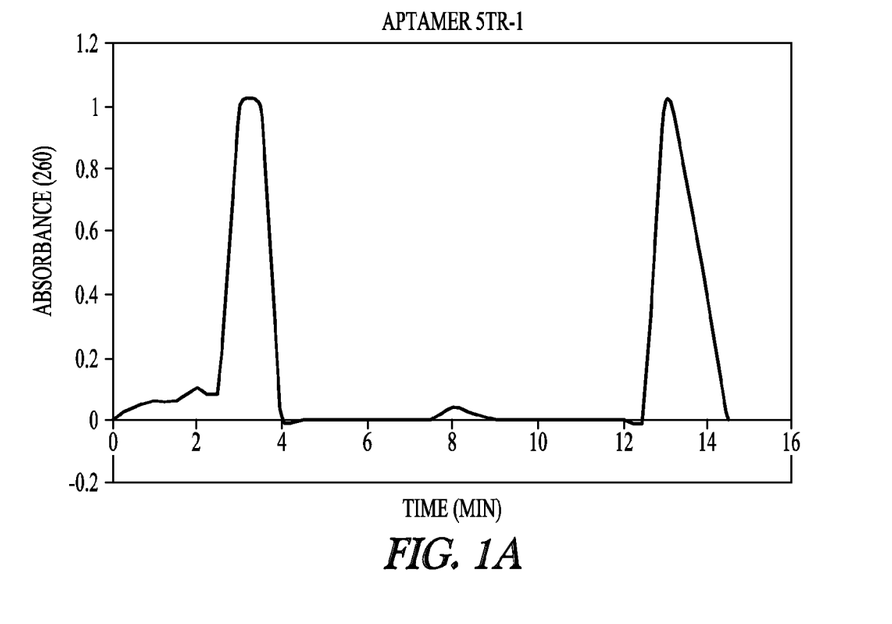
Figure 1B:
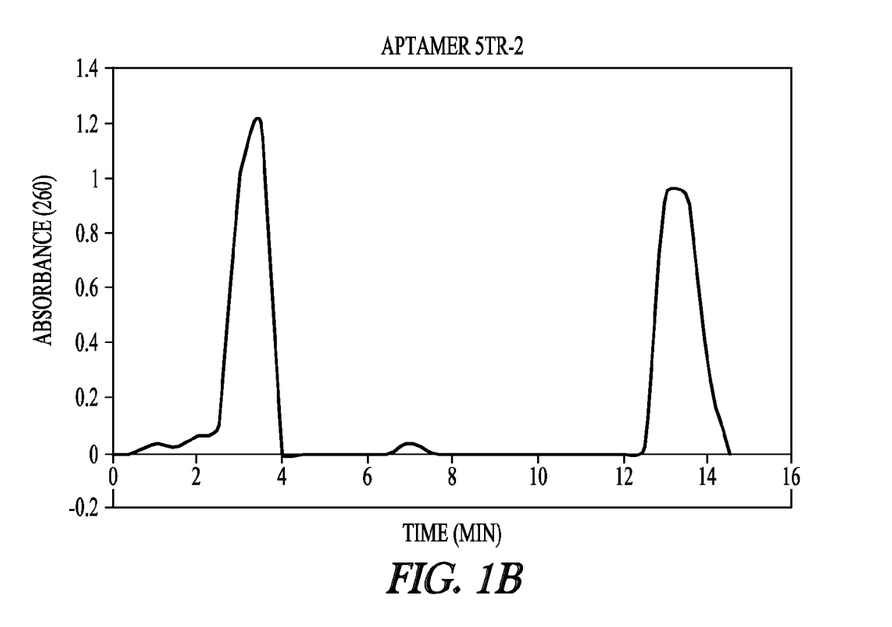
Figure 1C:
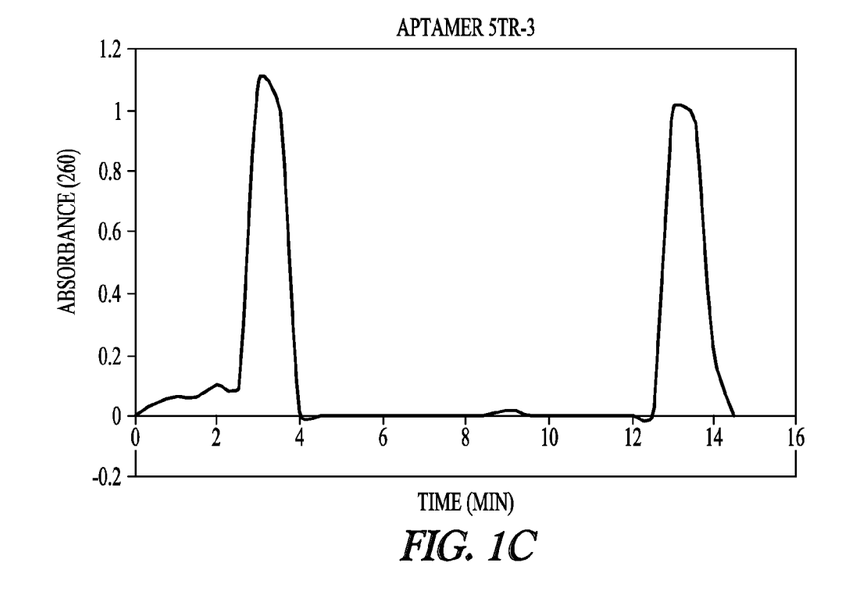
Figure 1D:
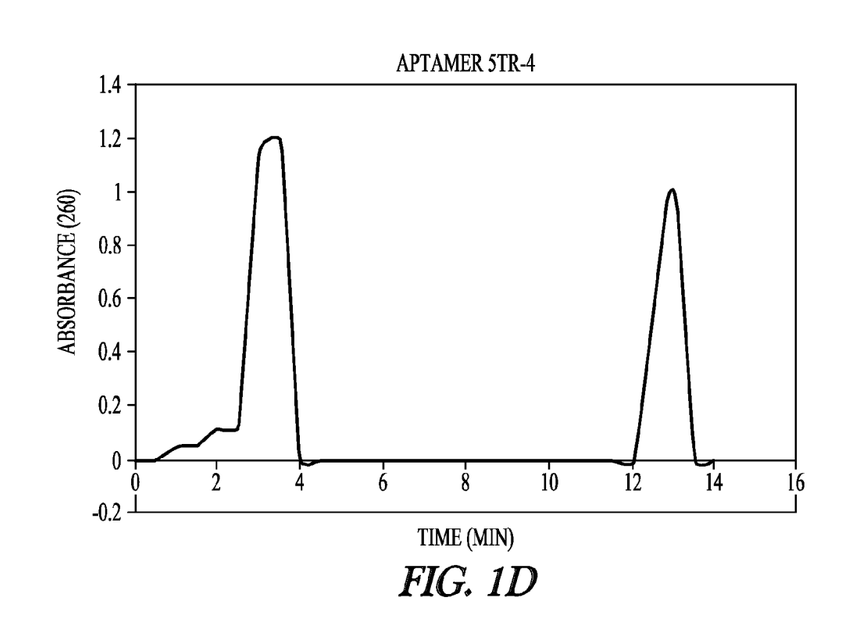
Figure 2:
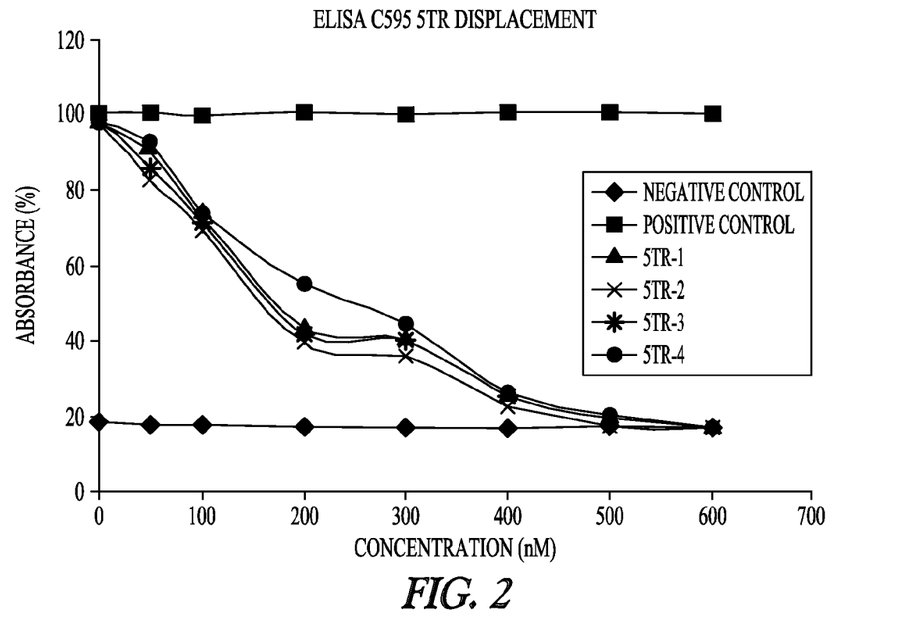
FIG. 2 shows % absorbance vs aptamer concentration from an ELISA test.

To verify the efficacy of the aptamer in binding to the MUC1 peptide and compete with the established anti-MUC1 antibody for epitope binding, we have used a previously described competition ELISA [Missailidis S, Thomaidou D, Borbas K E, and Price M R: Selection of aptamers with high affinity and high specificity against C595, an anti-MUC1 IgG3 monoclonal antibody, for antibody targeting. J Immunol Methods 2005; 296: 45-62]. To ascertain the ability of the aptamers to bind to the MUC1 peptide epitope and compete out the C595 antibody, the 5TR MUC1 recombinant protein was directly adsorbed onto the ELISA plate overnight. The commercially available C595 antibody was added to the ELISA in excess, to allow saturation and binding to all available peptide. Excess antibody was washed and the relevant aptamers were added to the wells at concentrations ranging between 0-600 nM. Colour was developed using a secondary, anti-mouse HRP conjugated antibody. As the peptide was immobilised at the wells of the ELISA plate, any antibody that remained bound to the peptide after the addition of aptamer would interact with the horseradish peroxidase-conjugated rabbit anti-mouse immunoglobulin leading to colour development. The antibodies that were competed out of the peptide, as aptamers bound to it, were removed in the various wash steps. The aptamers selected and tested in this ELISA have got variable base composition. A scrambled aptamer with base composition 7A, 5G, 7C, 6T has been previously shown not to interfere with the interaction between C595 and MUC1 peptide in this ELISA system [43]. The results (see FIG. 2) were plotted as % of Absorbance vs aptamer concentration.

The ability of the aptamers to displace the C595 antibody from its native antigenic protein appeared very similar between the selected aptamer species and approximately 200 nM of aptamer was enough to achieve 50% or more displacement of the antibody.

8. Characterisation of the 5TR-MUC1 Protein Interactions with Selected Aptamers Using SPR To quantify the interaction of the 5TR-MUC1 recombinant protein with the various selected aptamers and express it in the form of association and dissociation constants, we have utilised SPR on a BIAcore instrument. By plotting the changes of association (units of resonance) and time (seconds), experimental binding curves were obtained and association and dissociation constants were calculated.

In our experiments, the biotinylated 5TR-MUC1 protein was produced using the FluoReporter® Biotin-XX Protein Labelling Kit from molecular probes (USA). In brief, 5 mg of peptide was dissolved in 1 mL of carbonate buffer (0.1M sodium bicarbonate, pH 8.3) immediately before conjugation. Just before use, 2 mg of biotin-XX succinimidyl ester were dissolved in 0.1 mL DMSO at room temperature, vortexed until dissolved, added to the peptide solution as per manufacturer's specifications and allowed to incubate at room temperature for 2 hours. The solution was desalted in a PD-10 column (Pharmacia, Sweden) and tested for biotin levels according to manufacturer's positive indication kit procedure using the inherent properties of dye HABA (4'-hydroxyazobenzene-2-carboxylic acid). The levels were measured using UV absorption at 500 nm, according to manufacturer's specifications, and the difference in absorbance for the biotinylated peptide samples in relation to control (PBS) was calculated.

Biotinylated 5TR-MUC1 protein was immobilised on a BIAcore SA sensor chip (gold-streptavidin) and the system was optimised to reduce mass transport, steric hindrance, crowding, avidity and aggregation. A range of peptide concentrations, ranging from 1 µM to 1 nM were tested under different injection times and the optimum conditions used were 100 µL of 1 nM peptide in running buffer perfused over each individual channel at the rate of 25 µL/min for 60 sec pulse. Chip regeneration to peptide level was followed by the subsequent application of a 30 sec pulse with a solution of 10 mM NaOH. The aptamers were prepared in their selection buffers (phosphate buffer containing 100 mM NaCl, 5 mM MgCl$_2$, pH 7.4) at 1 µM and were applied with 30 sec injections with a 5 sec wash step with selection buffer to allow for non-specific analyte removal. The chip surfaces were regenerated (elution step) by the application of a 10 µL pulse of 1.5 M NaCl, 5 mM MgCl$_2$, pH 7.4.

Figure 3A:
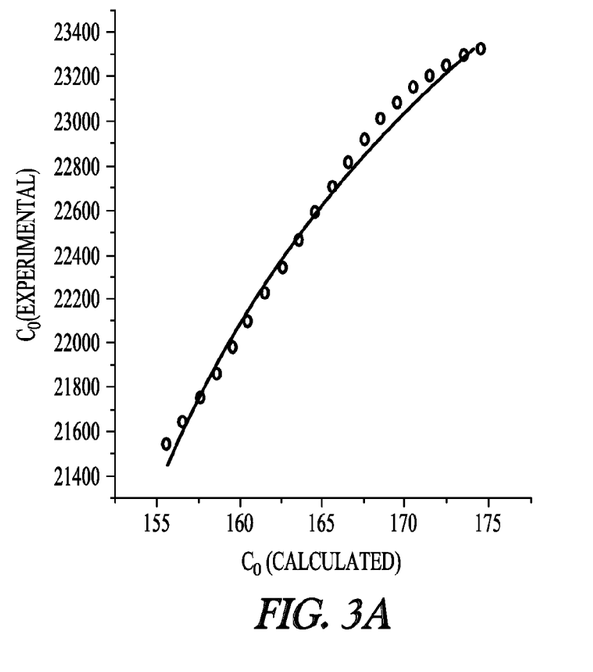
FIG. 3 shows curve fitting of an SPR experiment corresponding to recombinant human MUC1 protein-aptamer MUC1 5TR-1 interaction.
Figure 3B:
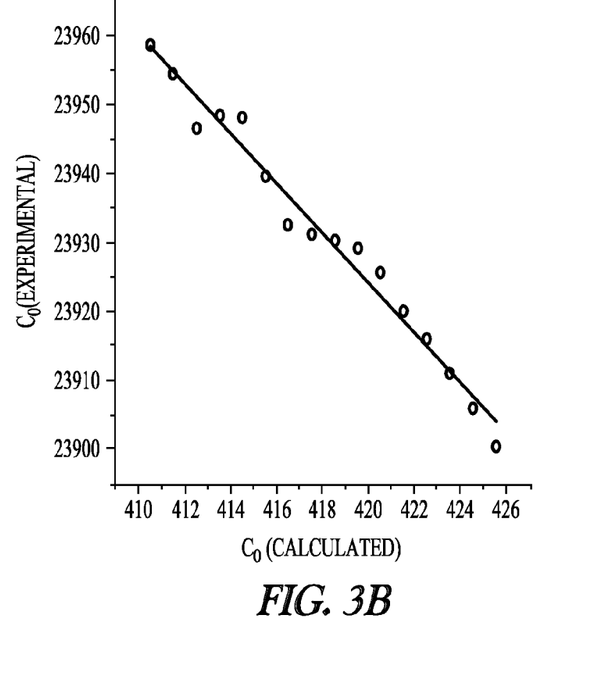

The experimental BIAcore data were fitted to two mathematical equations for the determination of association ($k_a$) and dissociation constants ($k_d$) using non-linear regression analysis. SPR sensograms representing the fast association and dissociation of the aptamers from their respective peptide targets are shown in FIG. 3 and fitted with Origin 6.0 (see FIG. 3).

The fast initial association phase was analysed by non-linear regression analysis of a one-phase exponential association model expressed by the following equation:

$$[\text{Response}] = [\text{Plateau}] + [\text{Span}](1 - \exp(-K(t - t_0))).$$

The dissociation phase was also subjected to non-linear regression analysis of a one-phase exponential association model expressed by the following equation:

$$[\text{Response}] = [\text{Bottom}] + ([\text{Plateau}] - [\text{Bottom}]) \exp(-k_d (t - t_0))$$

The concentration of free aptamer was assumed to be constant since an excess amount was applied to the system when compared to the amount of MUC1. Therefore K is the same as $k_a C + k_d$, where C was the total aptamer concentration in the system and the $k_a$ value was obtained from the following relationship: $k_a = (K - k_d)/C$. The $K_d$ was calculated from the following relationship: $K_d$ is equal to $k_d/k_a$. Data statistical fitting was represented as $X^2$.

FIG. 3 shows curve fitting of SPR experiment corresponding to recombinant human MUC1 peptide aptamer MUC1 5TR-1 interaction. The association (left) and dissociation plots (right) as analyzed by the Origin 6.0 graphing software. X axis $c_0$ (calculated) corresponds to time in seconds. Y axis $C_0$ (calculated) corresponds to RU units as given by BIAcore 2000 software.

Similar graphs were obtained for the remaining aptamers. Determined binding constants have been tabulated in Table 1.

TABLE 1

5TR-MUC1 recombinant protein: DNA aptamer binding analysis by SPR.

| Aptamer | Protein | $k_a$ (M$^{-1}$s$^{-1}$) | $k_d$ (s$^{-1}$) | $k_d$ (nm) | $X^2$ |
|---|---|---|---|---|---|
| MUC1 5TR-1 | 5TR MUC1 | $0.207 \times 10^7$ | 0.00098 | 47.3 | 0.984 |
| MUC1 5TR-2 | 5TR MUC1 | $1.488 \times 10^7$ | 0.01268 | 85.2 | 0.986 |
| MUC1 5TR-3 | 5TR MUC1 | $0.430 \times 10^7$ | 0.00358 | 83.0 | 0.981 |
| MUC1 5TR-4 | 5TR MUC1 | $0.45 \times 10^7$ | 0.00311 | 69.0 | 0.974 |

The SPR data have confirmed the high affinity of the aptamers for the 5TR-MUC1 protein in solution, with $K_d$ values in the nanomolar range.

6. Nickel NTA Glycoprotein-DNA Aptamer Interactions with the Glycosylated MUC1 5TR In order to assess the glycosylated MUC1 aptamer:glycoprotein interactions an assay was performed using the principle of His-tagged capture by the nickel magnetic agarose beads (as used in HiTrap chelating column). This assay allows for the rapid in tube detection/screening of aptamer binding to glycosylated peptide on a three step, binding:wash:partitioning, protocol.

The Qiagen kit containing agarose magnetic beads in the proportion of 5% solution coated with nickel for His-tag purification was used for the assay. Seven tubes each containing 900 µl of start buffer (100 mM $NaCl_2$, 5 mM $MgCl_2$, pH 7.4) used to resuspend a 10 µM solution of glycosylated MUC1 5TR peptide were prepared according to manufacturer's instructions:

10 µl of the 5% beads solution was added to the solution and incubated at 4° C. for half an hour with shaking. After 30 minutes, supernatant was removed. The beads were washed by adding start buffer, allowing 1-5 min of washing time. 1 mM (500 µl) of each Glycosylated MUC1 aptamer solution in start buffer were added to the previously prepared magnetic beads containing his-tagged glycosylated MUC1. The solution containing complexed beads and aptamer solution were allowed to incubate at 37° C. for 1 hour with shaking.

After one hour the supernatant was removed and its absorbance was measured using a UV spectrometer (Eppendorf, USA) at 260 nm. The remaining Magnetic beads were washed three times with 500 µl of wash buffer (150 mM $NaCl_2$, 5 mM $MgCl_2$, pH 7.4). The supernatant was removed and 50 µl of elution buffer (1.5M $NaCl_2$, 5 mM $MgCl_2$, pH 7.4) were added. The elution buffer was allowed to incubate with magnetic beads for 5 min with shaking. The magnetic beads were spun for 30 seconds at 4000 rpm to a pellet. The magnetic beads were attracted by a magnetic bar and supernatant was removed. The eluted supernatant was removed and measured using a UV spectrometer (Eppendorf, USA) 260 absorbance.

Figure 4A:
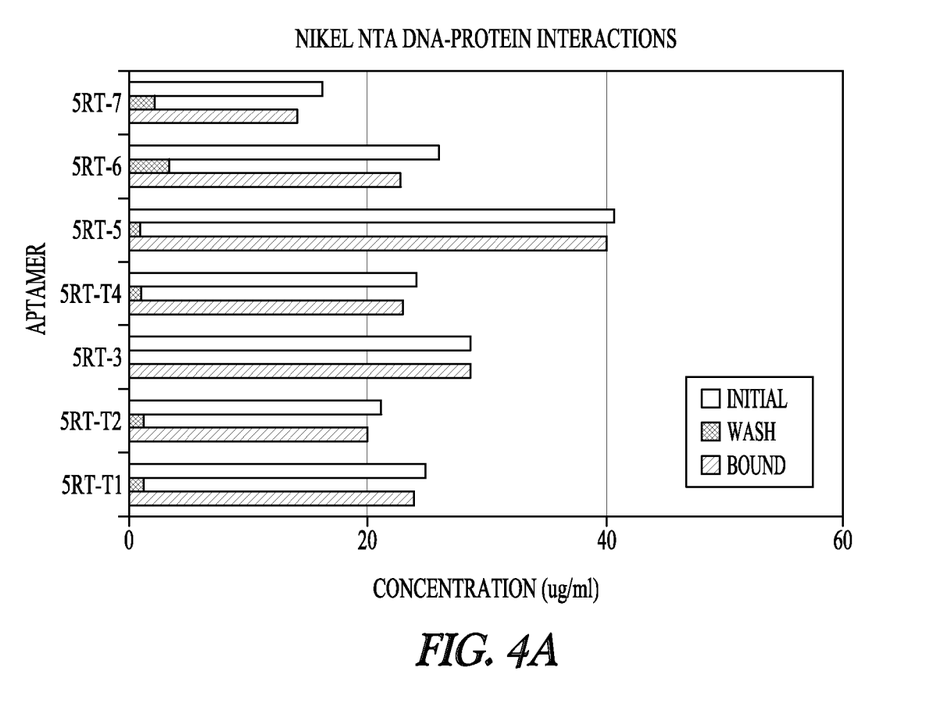
FIG. 4 shows a nickel NTA aptamer:Tn antigen interaction histogram.
Figure 4B:
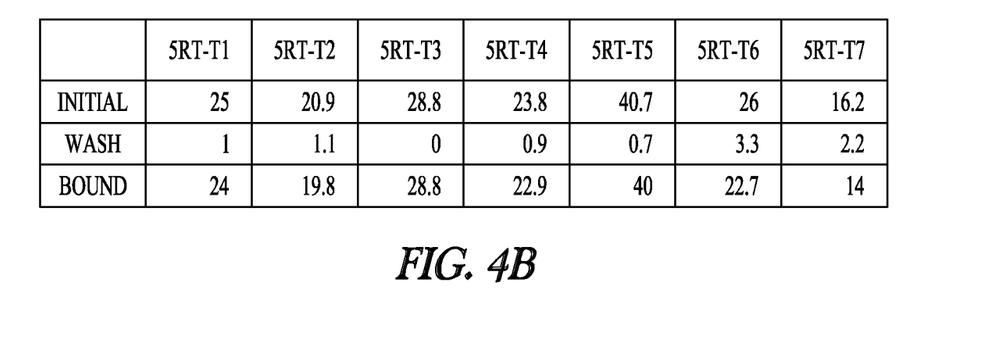

FIG. 4 shows the nickel NTA Aptamer:Tn antigen interaction Histogram showing initial DNA concentration, wash DNA concentration and final bound concentration as measured by 260 UV spectroscopy (Top) and results table (bottom).

CONCLUSION

From the series of all the above assays we can ascertain that all MUC1 5TR and glycosylated MUC1 5TR Tn antigen aptamers were analyzed and found to be good binders to their target, with the ability to bind selectively and with high affinity to their protein target and with the following aptamer sequences obtained.

MUC1 5TR, physiological, from bacteria (Most dominant) Non-Tn 5TR:

```
                                           (SEQ ID NO: 1)
     MUC1 5TR-1     GAAGTGAAAATGACAGAACACAACA (SEQ ID NO: 2)
     MUC1 5TR-2     GGCTATAGCACATGGGTAAAACGAC (SEQ ID NO: 3)
     MUC1 5TR-3     CAAACAATCAAACAGCAGTGGGGTG (SEQ ID NO: 4)
     MUC1 5TR-4     TACTGCATGCACACCACTTCAACTA
```

MUC1 5TR glycosylated, physiological, from bacteria, glycosylated with T1 (Sugar selection)

```
TR-T1   GGGTTATATTACTCGGCCGGTGTAA     (SEQ ID NO: 5)

5TR-T2  GGCTATAGCACATGGGTAAAACGAC     (SEQ ID NO: 6)

5TR-T3  GGCGTACGGTAGGCGGGGTCAACTG     (SEQ ID NO: 7)

5TR-T4  GCTGGGTAAATAGATGATTCCCGGC     (SEQ ID NO: 8)

5TR-T5  AGTGGTGGTTTTATAAGACTGATAC     (SEQ ID NO: 9)

5TR-T6  TAGCCTTAATGCCTTTGTAAGGCGA     (SEQ ID NO: 10)

5TR-T7  CGGTCTACGGAGCCGCGTTAAACTT     (SEQ ID NO: 11)
```

---

The invention claimed is:

1. An aptamer ligand to recombinant MUC1 comprising the sequence GGCGTACGGTAGGCGGGGTCAACTG (SEQ ID NO: 7).

2. The aptamer of claim 1 comprising one or more modified nucleotides.

3. The aptamer of claim 1 which is at least 25 nucleotides in length.

4. The aptamer of claim 1 consisting of SEQ ID NO: 7.

5. The aptamer of claim 1 which is a ligand to glycosylated MUC1.

6. The aptamer of claim 1 which has a greater binding affinity to glycosylated MUC1 than to unglycosylated MUC1.

7. The aptamer of claim 1 which has a greater binding affinity to recombinant MUC1 than to either or both of the 60-mer consisting of three copies of the repeat sequence APDTRPAPGSTAPPAHGVTS (SEQ ID NO: 12), or to the nine amino acid peptide APDTRPAPG (SEQ ID NO: 13).

8. The aptamer of claim 1 wherein the $K_d$ of the aptamer interaction with MUC1 is less than 1000 nM.

9. The aptamer of claim 1 in association with another active moiety.

10. The aptamer of claim 9 wherein the other moiety is a label.

11. The aptamer of claim 9 wherein the other moiety is a therapeutic agent.

12. The aptamer of claim 9 wherein the other moiety is a radiation source.

13. The aptamer of claim 9 wherein the other moiety is an antibody or fragment or portion.

14. An expression vector encoding an aptamer of claim 1.

15. A pharmaceutical composition comprising an aptamer as claimed in claim 1.

* * * * *

SEQUENCE LISTING

```
<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 1
gaagtgaaaa tgacagaaca caaca                                          25

<210> SEQ ID NO 2
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 2
ggctatagca catgggtaaa acgac                                          25
```

<210> SEQ ID NO 3
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 3
caaacaatca aacagcagtg gggtg                                            25

<210> SEQ ID NO 4
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 4
tactgcatgc acaccacttc aacta                                            25

<210> SEQ ID NO 5
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 5
gggttatatt actcggccgg tgtaa                                            25

<210> SEQ ID NO 6
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 6
ggctatagca catgggtaaa acgac                                            25

<210> SEQ ID NO 7
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 7
ggcgtacggt aggcggggtc aactg                                            25

<210> SEQ ID NO 8
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 8
gctgggtaaa tagatgattc ccggc                                            25

<210> SEQ ID NO 9
<211> LENGTH: 25
<212> TYPE: DNA
<213> ORGANISM: Artificial Sequence
<220> FEATURE:
<223> OTHER INFORMATION: A synthetic aptamer against MUC1

-continued

```
<400> SEQUENCE: 9
agtggtggtt ttataagact gatac                                              25

<210> SEQ ID NO 10
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 10
tagccttaat gcctttgtaa ggcga                                              25

<210> SEQ ID NO 11
<211> LENGTH: 25
<212> TYPE: DNA
<213> ORGANISM: Artificial Sequence
<220> FEATURE:
<223> OTHER INFORMATION: A synthetic aptamer against MUC1

<400> SEQUENCE: 11
cggtctacgg agccgcgtta aactt                                              25

<210> SEQ ID NO 12
<211> LENGTH: 20
<212> TYPE: PRT
<213> ORGANISM: Artificial Sequence
<220> FEATURE:
<223> OTHER INFORMATION: A synthetic MUC1 60-mer repeat sequence

<400> SEQUENCE: 12

Ala Pro Asp Thr Arg Pro Ala Pro Gly Ser Thr Ala Pro Pro Ala His
1               5                   10                  15

Gly Val Thr Ser
            20

<210> SEQ ID NO 13
<211> LENGTH: 9
<212> TYPE: PRT
<213> ORGANISM: Artificial Sequence
<220> FEATURE:
<223> OTHER INFORMATION: A synthetic MUC peptide

<400> SEQUENCE: 13

Ala Pro Asp Thr Arg Pro Ala Pro Gly
1               5
```